(12) United States Patent
Schweitzer, III et al.

(10) Patent No.: US 8,155,326 B2
(45) Date of Patent: Apr. 10, 2012

(54) SYSTEM, METHOD, AND APPARATUS FOR USING THE SOUND SIGNATURE OF A DEVICE TO DETERMINE ITS OPERABILITY

(75) Inventors: Edmund O. Schweitzer, III, Pullman, WA (US); David E. Whitehead, Pullman, WA (US); Timothy M. Minteer, Pullman, WA (US)

(73) Assignee: Schweitzer Engineering Laboratories, Inc., Pullman, WA (US)

( * ) Notice: Subject to any disclaimer, the term of this patent is extended or adjusted under 35 U.S.C. 154(b) by 824 days.

(21) Appl. No.: 12/247,736

(22) Filed: Oct. 8, 2008

(65) Prior Publication Data

US 2009/0091441 A1     Apr. 9, 2009

Related U.S. Application Data

(60) Provisional application No. 60/998,120, filed on Oct. 9, 2007.

(51) Int. Cl.
*H04R 29/00*     (2006.01)
(52) U.S. Cl. ............... 381/56; 381/57; 381/58; 381/59; 381/77; 381/80; 381/81; 381/71.1; 381/94.1
(58) Field of Classification Search .............. 381/56, 381/57, 58, 59, 77, 80, 81, 71.1, 94.1
See application file for complete search history.

(56) References Cited

U.S. PATENT DOCUMENTS

| 5,682,134 | A | 10/1997 | Stallbohm | |
|---|---|---|---|---|
| 7,750,814 | B2 * | 7/2010 | Fisher et al. | ............... 340/573.1 |
| 2004/0145467 | A1 * | 7/2004 | Roby et al. | ............... 340/531 |

* cited by examiner

*Primary Examiner* — Tan N Tran
(74) *Attorney, Agent, or Firm* — Eugene M. Cummings P.C.

(57) ABSTRACT

A system for monitoring the operation of one or more devices is provided. The system includes a microphone acoustically coupled to one the monitored device. An analog-to-digital-converter samples the microphone and a processor examines the resultant digital signal for the occurrence of an abnormal event.

17 Claims, 9 Drawing Sheets

SYSTEM, METHOD, AND APPARATUS FOR USING THE SOUND SIGNATURE OF A DEVICE TO DETERMINE ITS OPERABILITY

CROSS-REFERENCE TO RELATED APPLICATIONS

This application claims priority under 35 U.S.C. §119(e) from U.S. Provisional Patent Application No. 60/998,120, entitled "SYSTEM, METHOD, AND APPARATUS FOR USING THE SOUND SIGNATURE OF AN INTELLIGENT ELECTRONIC DEVICE TO DETERMINE ITS OPERABILITY," filed on behalf of inventors Edmund O. Schweitzer III, David E. Whitehead, and Timothy M. Minteer, all of Pullman, Wash., on Oct. 9, 2007, and which is hereby incorporated by reference in its entirety.

FIELD OF THE INVENTION

The present invention relates generally to systems, methods, and apparatus for determining the operational efficacy of various devices, and more particularly to systems, methods and apparatus of using the sound signatures from one or more pieces of mechanical, electrical, or electromechanical equipment, both in its quiescent state and during operation, to determine the operational efficacy and operational state of a monitored device.

DESCRIPTION OF THE PRIOR ART

Sound is always associated with some specific event, whether that event is a person speaking, a bird flapping its wings, or a motor spinning. Human beings naturally recognize certain sounds and associate them with specific occurrences. For example, every child learns to recognize the sound of her mother's voice. Another example, more apt to the disclosure, is that many auto-mechanics can diagnose a problem with a vehicle merely by listening to the vehicle in operation. These mechanics have learned to associate a sound signature with certain mechanical defects they have encountered in the past. While diagnosis of electro-mechanical devices, such as automobiles, is within general human experience, the use of this technique by prior art devices is sparse.

Listeners generally identify sounds by comparing them to sounds that a listener previously heard. For example, a particular word when spoken by a person with a reasonably normal vocal system makes a similar sound to the same word spoken by the vast majority of other individuals, thereby allowing a normal listener to recognize the spoken word. This is so despite the enormous variance in pronunciation, inflection, dialect, etc., which occurs from individual to individual. Correlation is a mathematical operation that can be used to determine the degree of similarity between two independent sets of numbers. There are a number of well-known ways to calculate correlation, such as, for example, the Pearson (Galton) product-moment correlation coefficient.

U.S. Pat. No. 5,682,134, filed on Jun. 10, 1996, uses a computer-based acoustic monitoring system to monitor the interior of an automobile, and detect when changes in the ambient sound signature take place. However, this system is only useful for detecting when the sound signature of the interior has changed, indicating an intrusion into the interior. It cannot diagnose problems with the automobile, like the auto-mechanic described above. Further, it only bases its decision-making on a single event, i.e., when the interior of the automobile is secured and the natural quiescent sound signature is present.

OBJECTS OF THE INVENTION

Accordingly, it is an object of this disclosure to provide a system, apparatus, and method for identifying the operational state of one or more pieces of mechanical, electrical, or electromechanical equipment based on its measured sound signature.

Another object of this disclosure is to provide a system, apparatus, and method for determining the operational efficacy of one or more pieces of mechanical, electrical, or electromechanical equipment based on its measured sound signature.

Other advantages of the disclosed invention will be clear to a person of ordinary skill in the art. It should be understood, however, that a system, method, or apparatus could practice the disclosed invention while not achieving all of the enumerated advantages, and that the protected invention is defined by the claims.

SUMMARY OF THE INVENTION

The disclosed invention achieves its objectives by providing a system for monitoring the operation of one or more devices for the occurrence of an abnormal event. The system includes one or more microphones, each acoustically coupled to one or more of the monitored devices. A microphone provides an analog electrical signal corresponding to sound waves proximate to the microphone. The analog signals are sampled by at least one analog to digital converter, which provides one or more digital signals corresponding to the sampled analog signals. The digital signals are examined by a processor to determine whether an abnormal sound is occurring.

When an abnormal sound is registered, the monitoring system will provide a notification through the operation of an alarm contact or through the generation of a network message. The notification may be an alarm, or merely a notification of an abnormal sound. The notification will generally include the microphone where the sound was detected, as well as the time and date of the occurrence.

Generally, the processor will store exemplary signals in a memory for comparison with acquired digital signals. Stored exemplary signals can include the ambient sound signature present at the microphone as well as the sound signatures of normal events, such as breaker operations, and abnormal events, such as arcing. The sound signatures may be captured at the installation with the aid of a user or through the use of an automation system. A pattern matching algorithm is used to determine whether or not an acquired digital signal matches a recorded exemplary event.

BRIEF DESCRIPTION OF THE DRAWINGS

Although characteristic features will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE ILLUSTRATED EMBODIMENT

Figure 1:
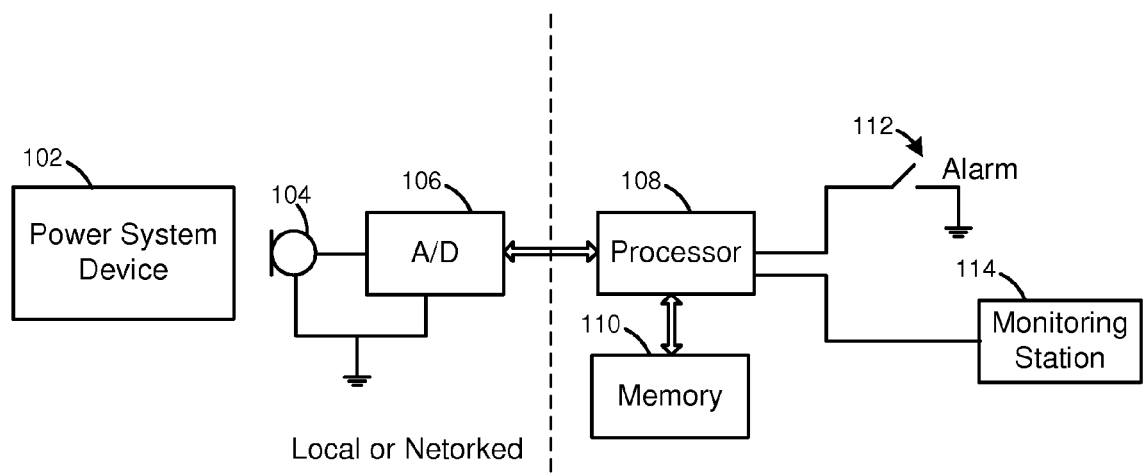
FIG. 1 is a simplified schematic diagram depicting one possible implementation of an apparatus implementing one aspect of the disclosure.

Turning to the Figures, and to FIG. 1 in particular, a power system device 102 such as, for example, a piece of mechanical, electrical, or electromechanical equipment, an intelligent electronic device ("IED"), or the like, is monitored by a microphone 104. The microphone 104 may be mounted directly to a sidewall of the power system device 102 by magnets, glue, tape, or some other mounting means. Alternatively, the microphone may be placed near a device to be monitored. The microphone produces an analog electric signal corresponding to a sensed audio signal. The electric signal is converted to digital form by analog-to-digital converter ("ADC") 106, which samples the signal at a constant frequency, such as 8 kHz. The microphone signal is acquired in accordance with well-known principles of analog signal acquisition to ensure that a usably clean signal is acquired. The digital signals are then stored by processor 108 in memory 110. When a sufficient time-period has elapsed, and a complete window of digital samples have been captured, a frequency spectrum could be derived through the use of Fast Fourier Transform ("FFT"), or other means. As digital signals are received, the processor 108 also analyzes the digital signals in both the time and frequency domain, as explained herein. In addition, one or more alarm contacts 112 could be coupled to the processor 108, and the processor 108 could communicate status to a monitoring station 114.

Figure 2:
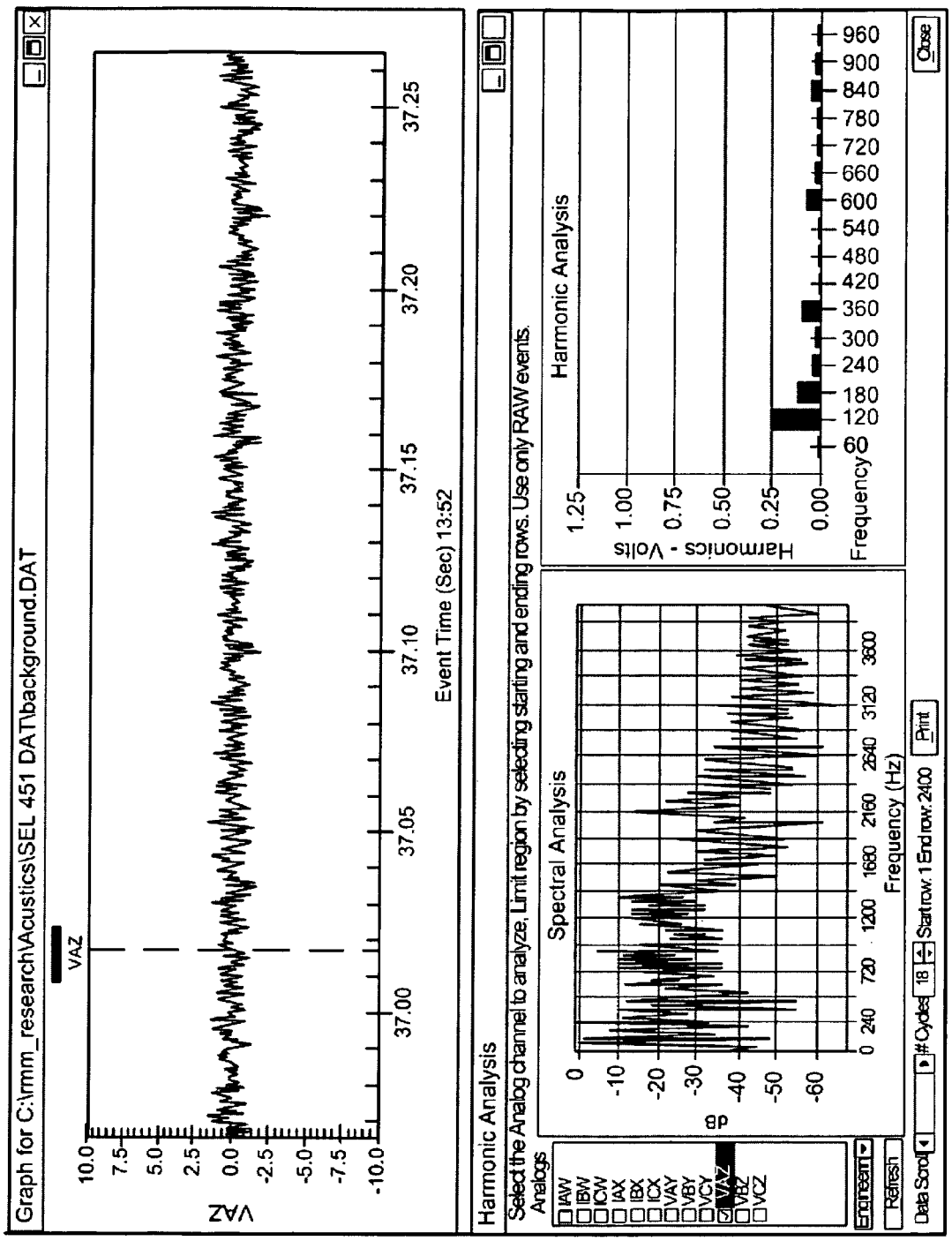
FIG. 2 is an approximately 300 ms snapshot of the audio signature of a power system device during its normal operating state.
Figure 3:
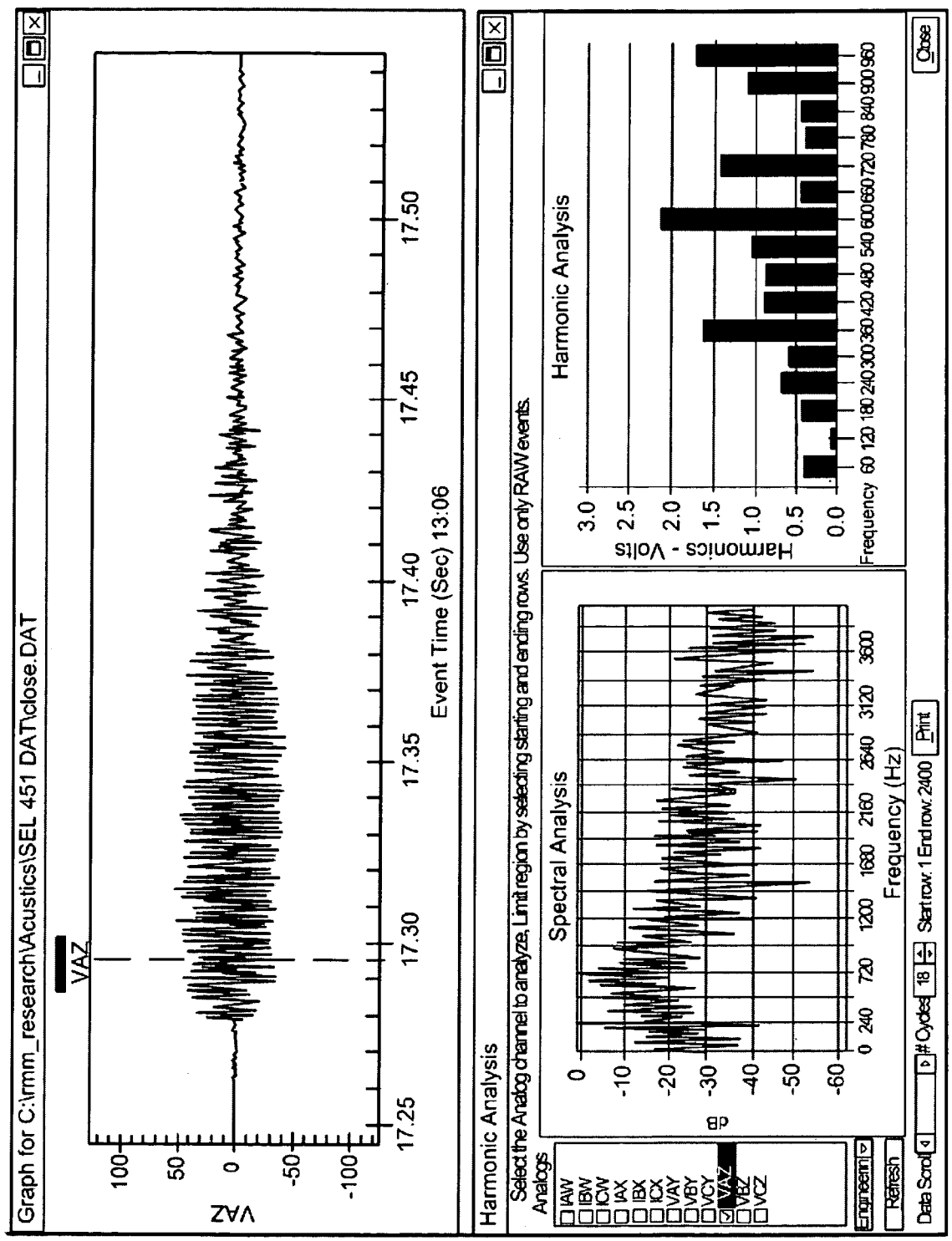
FIG. 3 is an approximately 300 ms snapshot of the audio signature of a power system device during the time that it is closing a breaker contact.
Figure 4:
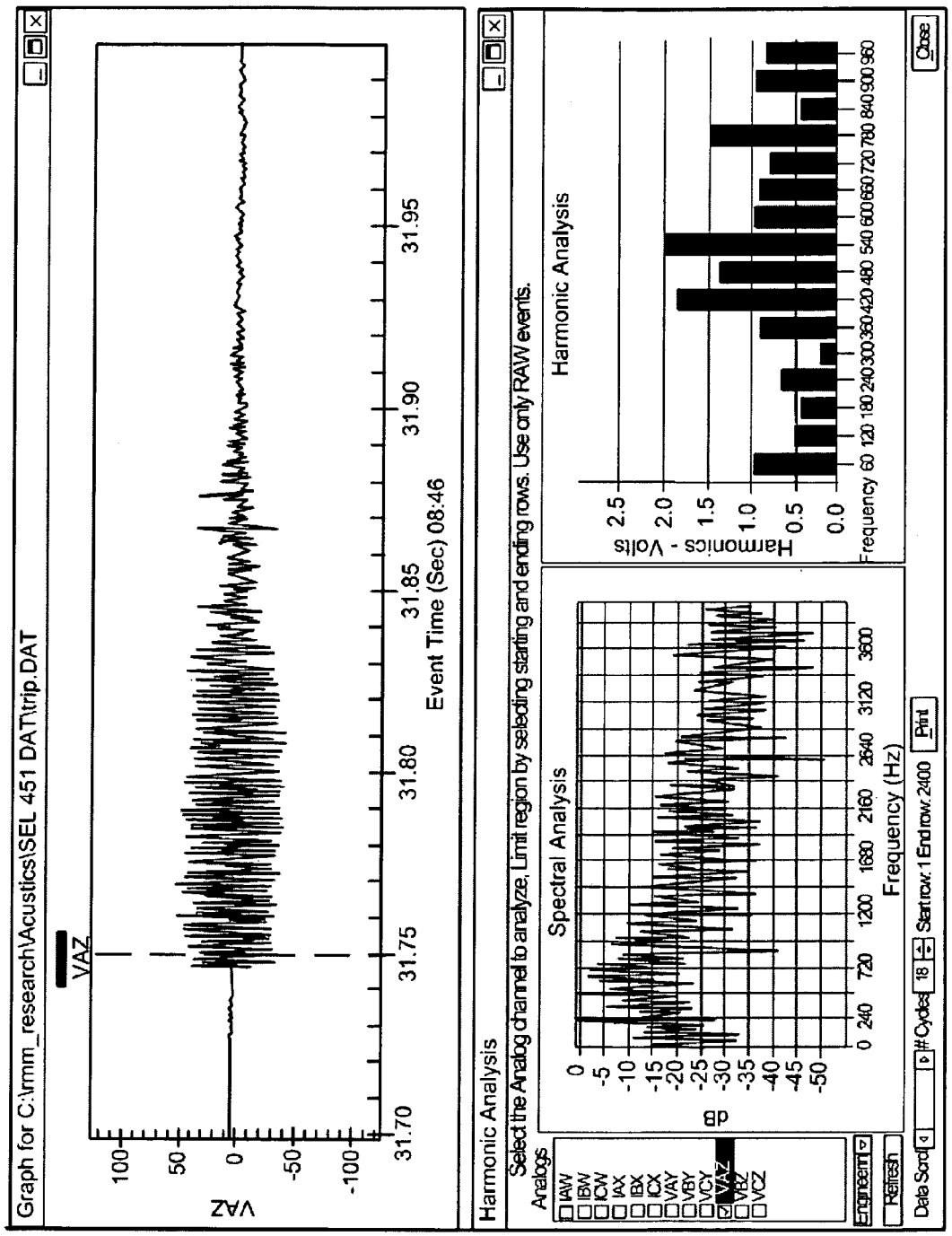
FIG. 4 is an approximately 300 ms snapshot of the audio signature of a power system device during the time that it is opening a breaker contact.
Figure 5:
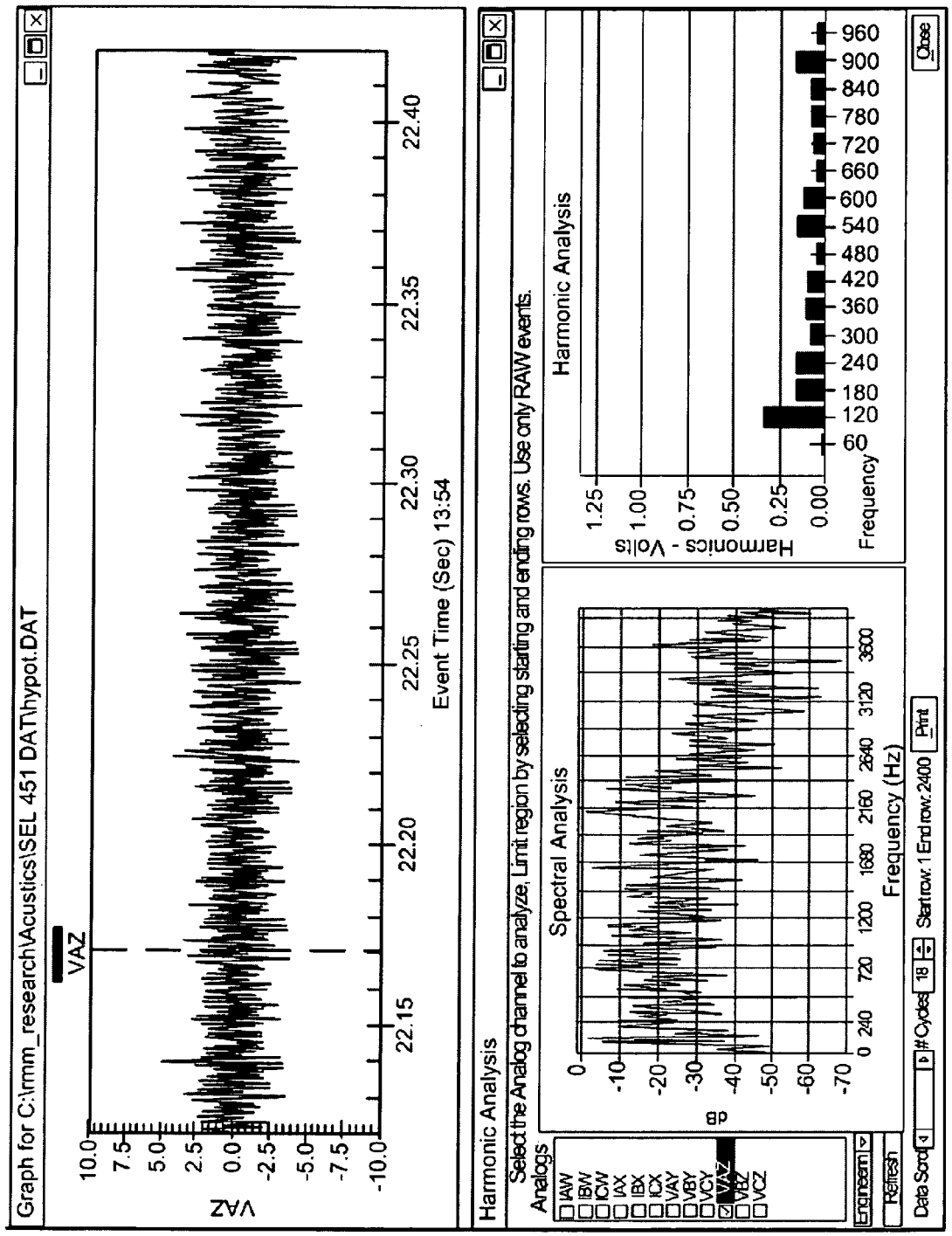
FIG. 5 is an approximately 300 ms snapshot of the audio signature of a power system device subjected to extremely high-voltage sufficient to cause dielectric breakdown.

Prior to operation of the disclosed audio monitoring system, various background measurements will have been made. For example, FIG. 2 depicts the ambient noise level of a monitored device; i.e., the noise level that is present at the installed device location when no event of concern, such as a trip or close operation, is occurring. This measurement could also be referred to as the ambient sound signature. In addition, specific events which are to be monitored for will also be recorded. FIG. 3 depicts a close operation for a monitored piece of electrical switchgear. FIG. 4 depicts a trip operation for the same piece of electrical switchgear. FIG. 5 depicts a pair of electrical wires subjected to voltage far beyond their carrying capacity, so that arcing occurs. FIGS. 2-5 include both a time domain depiction of the captured signal in the top half of the figure, and a frequency domain depiction of the captured signal in the bottom half of the figure.

A system embodying the disclosed invention could store digital representations of the signals depicted in FIGS. 2-5, and use those signals as exemplary models to determine if any of those events were presently occurring in a monitored system. Returning to FIG. 1, the processor would compare a recently captured time signal to the exemplary signal depicted in FIG. 2. The comparison could be in the time domain, or in the frequency domain. In particular, pattern matching algorithms could be applied to the time-domain representation of the captured signal as well as the frequency domain representation of the captured signal, and compared to the exemplary signal of FIG. 2. If a match was indicated with sufficient certainty, the processor would indicate that operation was proceeding normally. The same operation could be performed to determine if any of the events of FIGS. 3-5, i.e., contact closure, trip, or arcing, were occurring as well.

In a separate aspect of the disclosed invention, instead of using exemplary signals depicting a particular event to be monitored, the processor could use a mathematical model describing the audio signature associated with the event to be monitored.

Figure 6:
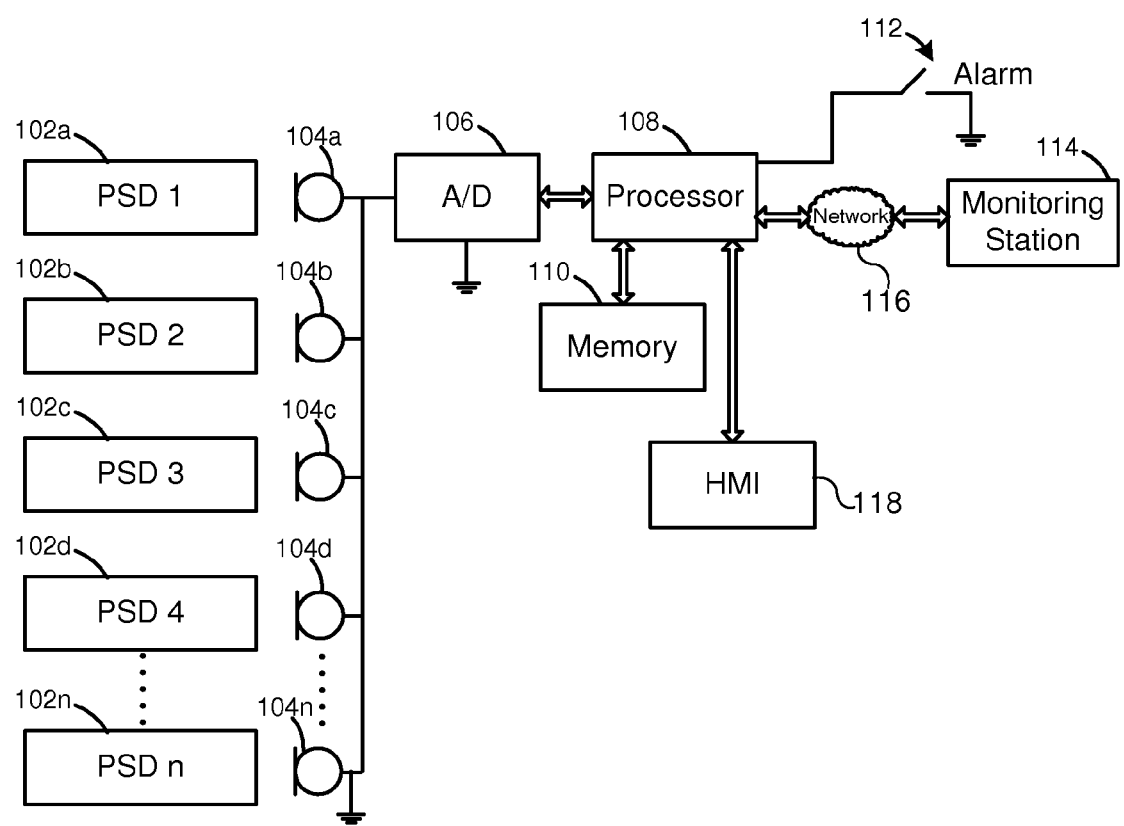
FIG. 6 is a simplified schematic diagram depicting another possible implementation of an apparatus implementing an aspect of the disclosure.

Turning to FIG. 6, an alternate implementation of the disclosed invention is pictured. A number of power system devices 102a-102n are monitored by a number of microphones 104a-104n. Generally, each device is monitored by a separate microphone to best capture the audio signature of that particular device. However, in certain circumstances, a single microphone could be positioned to monitor multiple devices. The audio signals acquired by the microphones 104a-104n are then converted to digital format by Analog to Digital Converter ("ADC") 106. In the embodiment depicted by FIG. 6, a single ADC is shown, with the signals from the microphones switched through an analog switch (not shown) and sampled by the ADC. However, it should be understood that multiple ADCs could be used instead, which would eliminate the need for an analog switch. The acquired digital signals are then examined by processor 108. While generally the IEDs will be collocated within the same facility, it is conceivable that audio signatures from devices located in different facilities could be acquired by a microphone, sampled by an ADC, and broadcast via a network to a computer or microprocessor 108.

The processor 108 will generally require some amount of memory 110 to store acquired samples, as well as to use for storing variables used in calculations, etc. The memory 110 may be integrated into processor 108, or separate from it. In accordance with the methods disclosed herein, the processor 108 can generate an alarm event causing alarm contact 112 to be closed, or broadcasting an alarm network event to network 116 as well as monitoring station 114. Audio samples can also be streamed to the monitoring station 114 using the network 116 so that a user can monitor the sound present at the microphone 104a-104n. The audio could also be stored to a storage device present at the monitoring station 114 for later listening. This would enable a user to listen at the monitoring station 116 to the sounds that caused a alarm network event prior to sending out a technician to deal with the event, thereby preserving resources by preventing "false alarms." A Human Machine Interface ("HMI") 118 is used to capture user settings and to initialize the audio monitor for operation in a given location.

Figure 7:
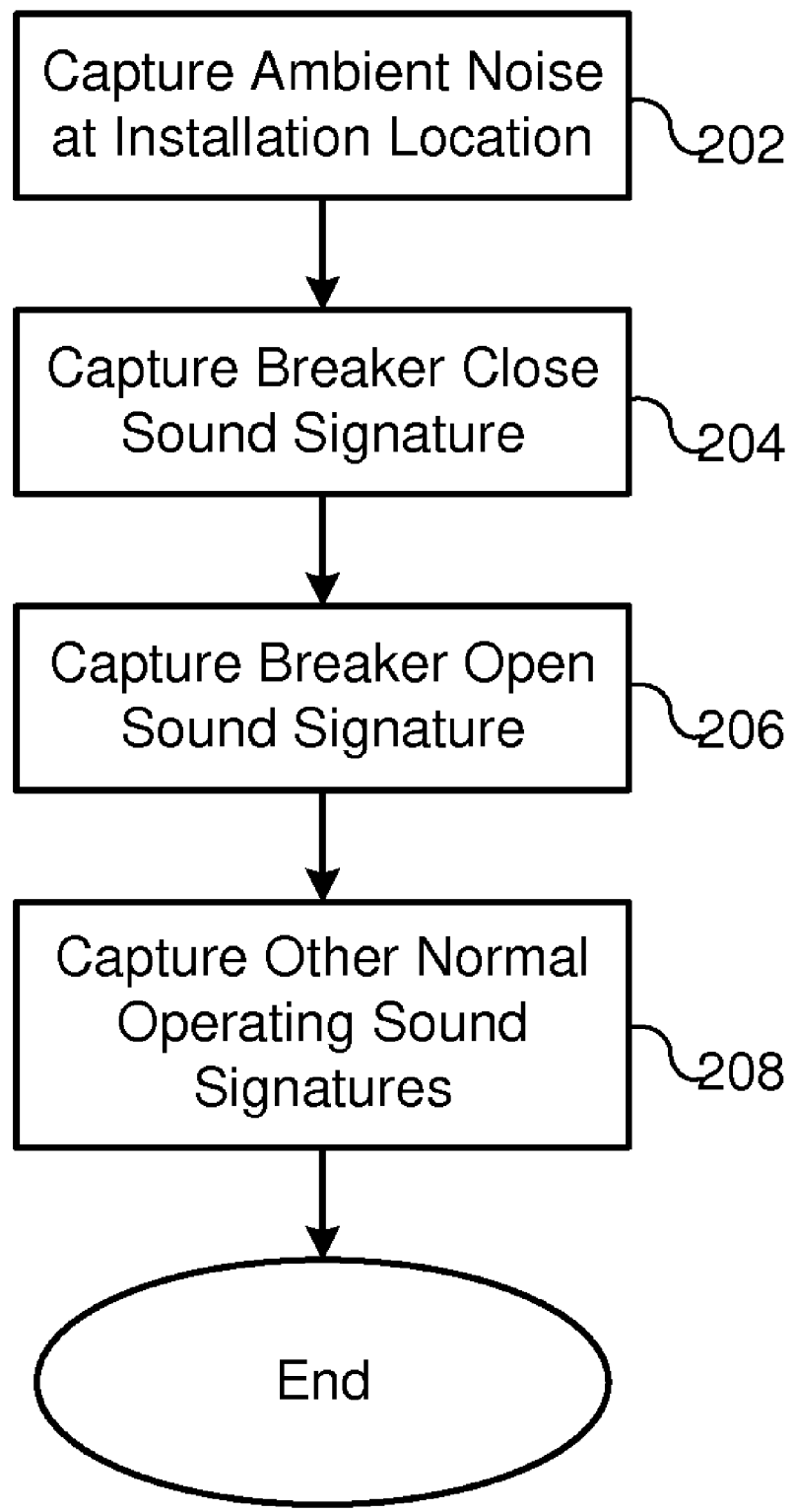
FIG. 7 is a flowchart depicting how a sequence of audio waveforms can be captured for use as exemplary sample windows by an apparatus.

Besides general settings, the disclosed audio monitoring system can record or otherwise capture certain audio signatures describing the operation of a device to be monitored as well as the ambient, or usual, noise occurring around the device to be monitored. A user could assist the audio monitoring system in capturing these events by using the HMI 118. For example, the HMI 118 could present the user with instructions, directing the user to produce certain events corresponding to the steps of FIG. 7. Turning to FIG. 7, a sequence of potential events is outlined. These events correspond to a typical power substation, which could include, for example, a monitoring intelligent electronic device, such as a distance relay, which controls one or more circuit breakers protecting a power line segment. This installation and the corresponding steps described below are intended to provide an example of the types of systems that could be monitored as described herein, and are not intended to limit the disclosed invention beyond any limitations expressed in the claims. In step 202, the ambient noise signature of the installation is captured. In step 204, a breaker close operation is initiated, and the corresponding sound signature is captured. In step 206, the sound signature of a breaker open operation is captured. Finally, any other normal operation sound signatures capable of being picked up by the monitoring system are recorded and appropriately labeled in step 208.

While a user could cause test operations in response to directions presented by the monitoring system's HMI, other methods could be used to capture the ambient sound signature and the sound signatures of normal events. For example, the monitoring system could issue network commands to connected devices causing various normal operations to occur. Automation protocols, such as IEC 61850, could be used to implement such functionality.

Figure 8:
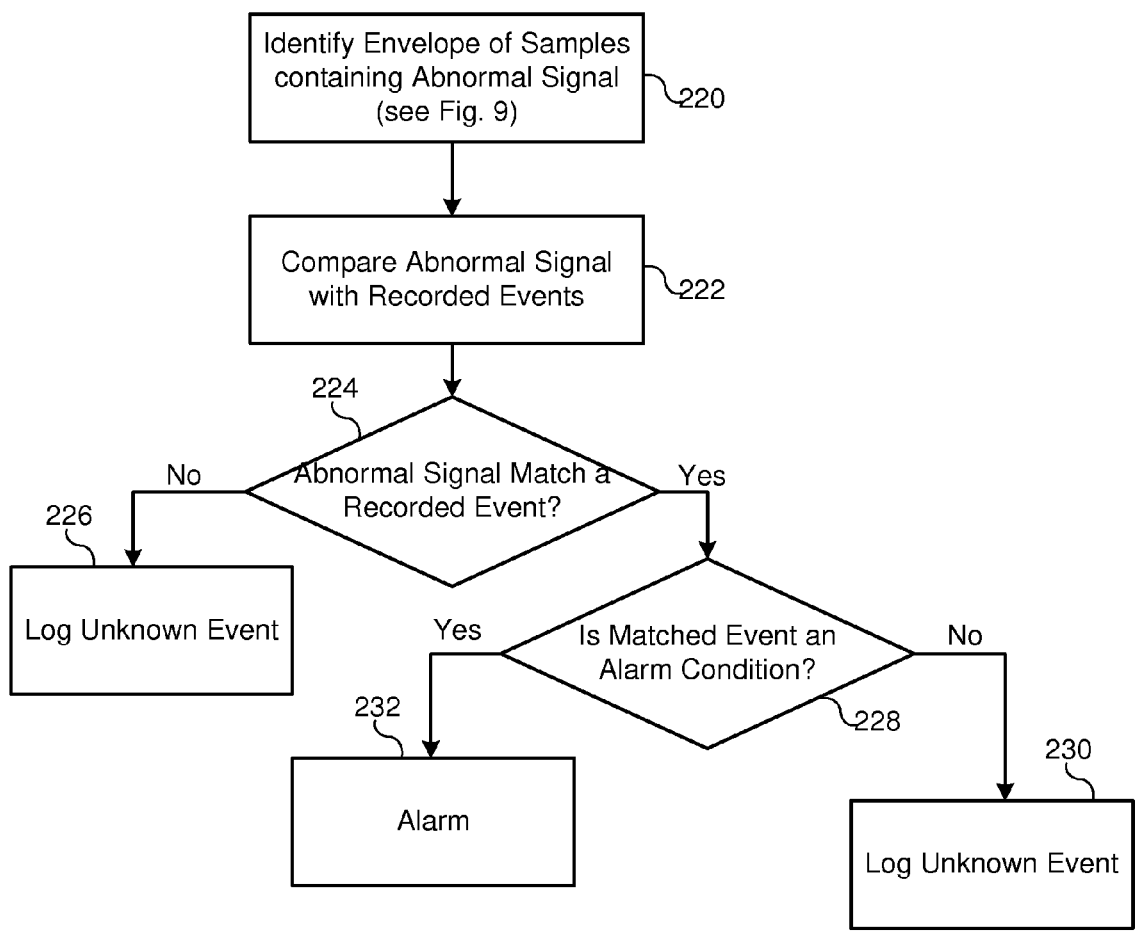
FIG. 8 is a flowchart depicting the normal operation of an apparatus implementing an aspect of the disclosure.

Turning to FIG. 8, a possible set of steps used to implement the normal operation of the disclosed monitoring system is depicted. In step 220, an envelope of samples containing an abnormal signal is identified. The identification of an abnormal signal is further explored in FIG. 9; however, an abnormal signal is most generally defined as any signal that does not correspond to the normal ambient sound signature recorded by a particular microphone. In step 222, the abnormal signal is compared with recorded sound signatures from known events, such as a breaker close event, a breaker open event, or the sound of an exemplary model of the monitored device being exposed to very high voltage. In step 224, a determination is made as to whether the abnormal signal matches any recorded events. If not, an unknown event is logged in step 226. However, depending on how the monitoring system is configured, an alarm event can be triggered or an alarm network event generated. If the abnormal signal does match a recorded event, a determination is made in step 228 as to whether the recorded event is an alarm condition. If not, a known event is logged in step 230. However, if the recorded event is an alarm condition, an alarm event is logged, and triggered in step 232. Note that the triggering of the alarm event could result in the closure of a relay contact or in the network transmission of an alarm message.

Figure 9:
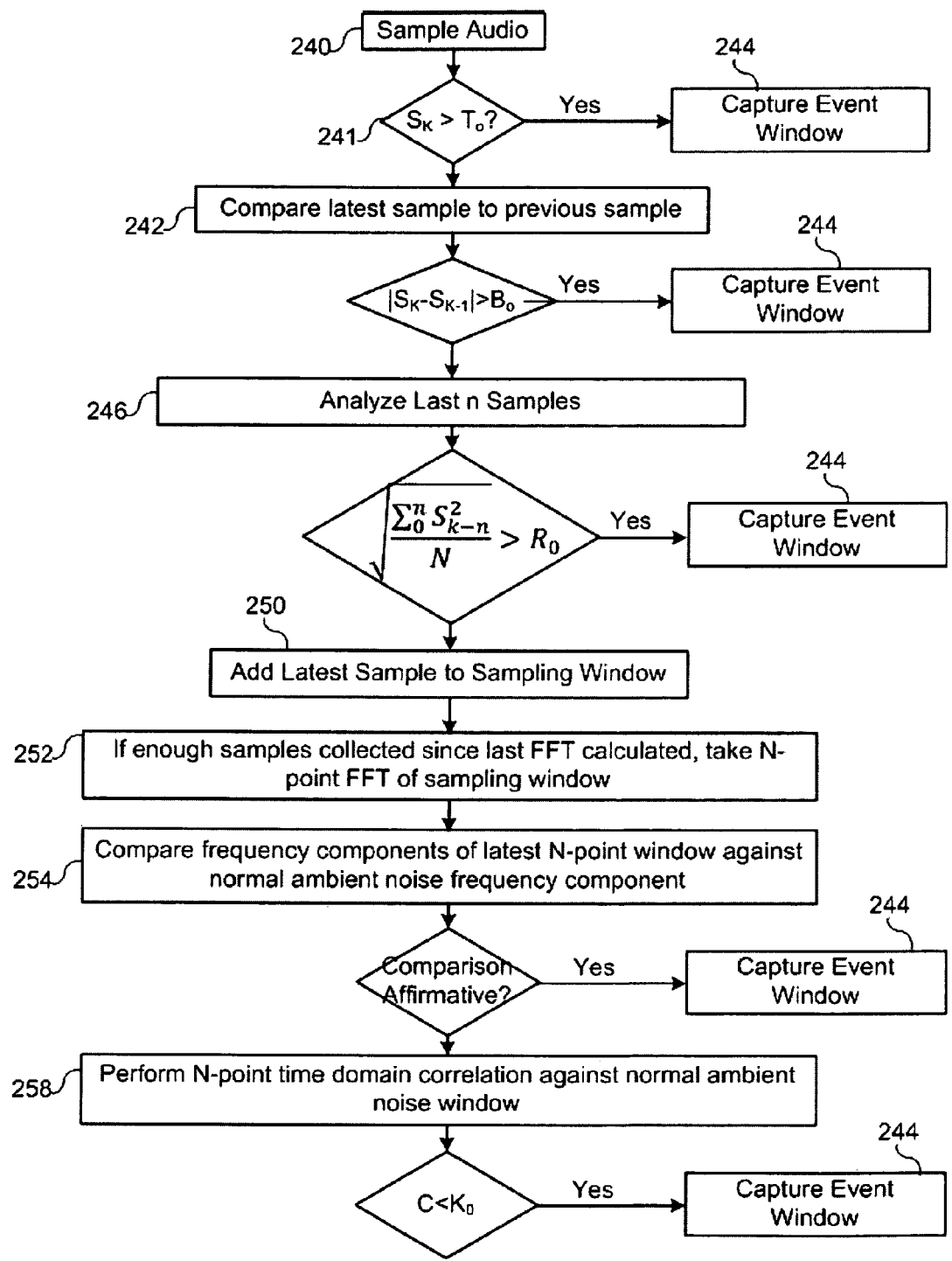
FIG. 9 is a flowchart depicting how the capture of an event window could be instantiated by an apparatus implementing an aspect of the disclosure.

FIG. 9 depicts a set of steps that a system implementing the disclosed invention may execute to identify an abnormal signal. As discussed earlier, the audio signal present at a microphone may be sampled periodically, and some number of preceding samples may be stored for use in calculations. In step 240, a sample is taken. This sample is compared to a threshold T0 in step 241. The threshold T0 may be (1) a factory programmed value based on, for example, the maximum output of the microphone, (2) a user programmed value, based on the user's judgment regarding usual decibel levels experienced by the installation, (3) a value programmatically determined and adjusted by the monitoring device based on, for example, the average decibel level of background noise in the installation. If the comparison is positive, meaning that the most recent sample Sk exceeds the threshold T0, an abnormal event capture window is initiated. The event capture window could be terminated based on a later sample having a value below a second threshold T1, or the lapse of a specific period of time, such as 300 milliseconds.

In step 242, the most recent sample Sk is compared with the previously taken sample, Sk−1. If the difference between the values of the samples exceeds a threshold B0, an event window is captured in step 244. The value B0 can be assigned or calculated in any of the ways enumerated above regarding the calculation of the threshold T0. In step 246, the root-mean-square ("RMS") value of the captured signal is calculated for the last N samples, and compared to (1) a threshold R0, and (2) previous RMS calculations for the acquired audio signal. If the comparison is positive, an event capture window is instantiated in step 244.

In step 250, the latest sample is added to a sampling window having a fixed number of samples. Step 252 involves the periodic computation of a Fast Fourier Transform, or some other frequency spectrum calculating method, such as the general Discrete Fourier Transform, the general Z-Transform, the Chirp Z-Transform, the Segmented Chirp Z-Transform, or other methods of calculating a Discrete Fourier Transform or Z-Transform. The calculation of a frequency calculation generally requires some number of samples, such as 1024 or 4096. Therefore, a new FFT will be calculated every 1024, 4096, or some other fixed number of samples. Accordingly, in step 252, if enough samples have been collected since the last calculation of a FFT, a new FFT is calculated, and a frequency spectrum is derived from the calculated FFT.

The calculated frequency spectrum can be examined in a number of different ways to determine if an abnormal event is occurring. One way would be to examine the calculated frequency spectrum for whether content at a particular frequency exceeded a threshold. Another way to examine the calculated frequency spectrum would be to check for a change from one calculated frequency spectrum to another at each frequency available within the calculated spectrum. Yet another way would be to compare each frequency component within the calculated frequency spectrum with the corresponding frequency components within the frequency spectrum of the "normal" noise signal observed by monitoring device; i.e., the ambient sound signature of the installation. For example, in FIG. 9, step 254 performs a correlation of the calculated frequency spectrum against the frequency spectrum of the ambient noise signature. If the correlation C is less than a particular threshold, such as 0.8, an abnormal event capture window is instantiated in step 244. Similarly, in step 258, a time domain correlation of the most recent sampling window is performed against the captured ambient noise signature, and if the correlation C is less than a given threshold K0, an event capture window is instantiated in step 244.

It should be understood that certain terms have been used throughout this disclosure to denote general concepts. For example, the term processor should be interpreted to include any device capable of making a mathematical computation, such as, for example and without limitation, a microprocessor, a microcontroller, a digital signal processor, a standalone computer, a networked computer, a distributed computer, a field programmable gate array, a complex programmable logic device, and numerous other specific types of devices would be included within this definition.

The foregoing description of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed is:

1. A system for monitoring the operation a power system device for the occurrence of an abnormal event comprising:
   i) a microphone acoustically coupled to the power system device, the microphone producing an analog signal corresponding to sound waves observed by the microphone;
   ii) an analog-to-digital converter for receiving the analog signal and producing a digital signal corresponding to the analog signal;
   iii) a processor comprising a memory, configured to:
      receive the digital signal;
      record in the memory a normal event sound signature corresponding to an operation of the power system device; and,
      determine whether the abnormal event has occurred.

2. The system of claim 1 further comprising an alarm contact coupled to the processor, the alarm contact for operation when the abnormal event is detected.

3. The system of claim 1 further comprising a network interface coupled to the processor, the network interface for generating a network message when the abnormal event is detected.

4. The system of claim 1 further comprising a first network interface coupled to the analog-to-digital converter and a network, and a second network interface coupled to the processor and the network, and wherein the processor receives the digital signal via the network.

5. The system of claim 1 wherein the processor
   records in the memory an ambient sound signature.

6. The system of claim 5 further comprising Human Machine Interface coupled to the processor, the Human Machine Interface providing instructions to a user enabling the recordation of the ambient sound signature and the normal event sounds signature.

7. The system of claim 5 wherein the processor compares the digital signal to the ambient sound signature using a pattern-matching algorithm to determine if the abnormal event has occurred.

8. The system of claim 7 wherein the digital signal consists of a latest sample and a plurality of previously stored samples, all of the samples generated periodically by the analog-to-digital converter, and wherein the processor further captures an event window consisting of a plurality of samples if a condition is met.

9. The system of claim 8 wherein the processor compares the latest sample to a threshold, and the processor captures the event window if the latest sample exceeds the threshold.

10. The system of claim 8 wherein the processor compares the latest sample to a previously acquired sample, and the processor captures the event window if the latest sample exceeds the previously acquired sample by a threshold.

11. The system of claim 8 wherein the processor calculates a root-mean-square value based on the latest sample and the previously stored samples, and compares the root-mean-square value to a threshold, and the processor captures the event window if the root-mean-square value exceeds the threshold.

12. The system of claim 8 wherein the processor calculates a first frequency spectrum describing a plurality of frequency components present in the digital signal, and wherein the processor compares the plurality of frequency components of the first frequency spectrum to a plurality of frequency components of a second frequency spectrum, the second frequency spectrum calculated prior to the calculation of the first frequency spectrum, and wherein the processor captures the event window if a frequency component of the first frequency spectrum differs from a corresponding frequency component in the second frequency spectrum by a threshold.

13. The system of claim 8 wherein the processor calculates a first frequency spectrum describing a plurality of frequency components present in the digital signal, and wherein the processor compares the plurality of frequency components of the first frequency spectrum to a plurality of frequency components of a second frequency spectrum, the second frequency spectrum calculated based on the recorded ambient sound signature, and wherein the processor captures the event window if a frequency component of the first frequency component of the first frequency spectrum differs from a corresponding frequency component in the second frequency spectrum by a threshold.

14. The system of claim 8 wherein the processor determines a correlation of the digital signal to the ambient sound signature and wherein the processor captures an event window if the correlation is less than a threshold.

15. The system of claim 1 further comprising a network interface coupled to the processor, wherein the processor
   (1) accesses a database describing another power system device installed proximate to the system for monitoring, and
   (2) operates the network interface to generate a sequence of network messages for operating the another power system device.

16. The system of claim 1 wherein the processor further compares the digital signal to the normal event sound signature using a pattern matching algorithm to determine if the digital signal corresponds to the normal event sound signature.

17. The system of claim 16 wherein the processor logs a normal event in the memory if the digital signal corresponds to the normal event sound signature.

* * * * *